(12) United States Patent
Ehbets

(10) Patent No.: US 6,844,931 B2
(45) Date of Patent: Jan. 18, 2005

(54) SPECTROPHOTOMETER AND ITS USE

(75) Inventor: Peter Ehbets, Zürich (CH)

(73) Assignee: Gretag-Macbeth AG, Regensdorf (CH)

( * ) Notice: Subject to any disclaimer, the term of this patent is extended or adjusted under 35 U.S.C. 154(b) by 8 days.

(21) Appl. No.: 10/303,335

(22) Filed: Nov. 25, 2002

(65) Prior Publication Data
US 2003/0169421 A1 Sep. 11, 2003

(30) Foreign Application Priority Data
Nov. 26, 2001 (EP) .......................... 01127427

(51) Int. Cl.[7] .................................. G01J 3/42
(52) U.S. Cl. ........................ 356/328; 356/406
(58) Field of Search .................. 356/319, 326, 356/328, 419, 402, 406, 407

(56) References Cited
U.S. PATENT DOCUMENTS

| 4,969,037 A | 11/1990 | Poleschinski et al. |
| 6,147,761 A | 11/2000 | Walowit et al. |
| 6,332,573 B1 * | 12/2001 | Gu et al. ............ 235/462.06 |
| 6,369,895 B1 * | 4/2002 | Keeney .................. 356/419 |

FOREIGN PATENT DOCUMENTS

| EP | 0144188 | 6/1985 |
| EP | 1072884 | 1/2001 |
| WO | 00/40935 | 7/2000 |
| WO | 01/29542 | 4/2001 |

OTHER PUBLICATIONS

European Search Report dated Apr. 29, 2002 in German (no translation).

Fletcher, "High Efficiency", Optics and Photonics News, Optical Society of America, Washington, D.C., US, Apr. 1999, pp. 18–23.

* cited by examiner

Primary Examiner—F. L. Evans
(74) Attorney, Agent, or Firm—McCarter & English, LLP

(57) ABSTRACT

A spectrophotometer including an optical measurement head, a spectrometer and a control electronic. The measurement head is equipped with a multi-channel illumination arrangement having exclusively light emitting diodes as spectrally continuous light source. Each illumination channel includes a light emitting diode, whereby each light emitting diode is separately controllable. In combination with the control electronic, an illumination with electronically adjustable spectral characteristics is hereby realized.

18 Claims, 9 Drawing Sheets

SPECTROPHOTOMETER AND ITS USE

FIELD OF THE INVENTION

The invention relates to a spectrophotometer, a densitometer and their use and application.

BACKGROUND ART

In modem digital processes for the reproduction of color documents, pictures and packages, desktop publishing and color management have become progressively more important. In desktop publishing, the designer these days generates on his computer in electronic form not only the graphic concept and the color design, but specifies progressively more of the reproduction technological parameters concerning the final production and multiplication of the document, such as, for example, the printing process, the paper quality or special colors. Since test prints are expensive and time consuming, it is desired for this application that the designer can simulate and test the color reproduction properties of his electronic design according to a special printing process.

The communication and reproduction of consistent colors is made possible by the use of color management technologies. In one color management system (CMS), the input and output systems involved in the workflow are calibrated and characterized with respect to color measurements with the use of color measurement apparatus. The connection between absolute measured color values and system specific color control signals is stored in so called apparatus profiles. Color information can be communicated and reproduced across different media and systems by the combination of device profiles.

The construction of existing color management systems has been standardized and described by ICC (International Color Council; see, for example http://www.imaging.org for the newest version of the ICC standard) and is summarized in the publication of the company Logo GmbH, a corporation of the GretagMacbeth Group in August 1999 under the title "Post Scriptum on Color Management, Philosophy and Technology of Color Management", by the authors Stefan Brnes, Liane May and Dietmar Fuchs.

By using color management and device profiles, the designer has the opportunity to visualize on his screen the color reproduction of different printing processes, or to simulate it with a digital printer. However, the options and the precision of such digital test methods are still limited at this point in time. Material or process specific parameters which influence the visual color perception, but can be captured not at all or only badly with the actually used color measurement devices generate difficulties for a correct visualization. Typical examples are substrate materials with differing surface properties, optical brighteners, or fluorescent colors.

Samples of the same color but with different surface properties have different appearances. A sample with a glossy surface is perceived darker and of more saturated color than one with a diffusely reflecting surface.

The effect of optical brighteners and fluorescent colors strongly depends on the illumination spectrum. For a correct evaluation, the light source in the measurement apparatus must be able to be adapted to real observation conditions.

So called effect color layers based on metallic or pearlescent pigments are of increasing importance for packaging and advertising. They are distinguished by strongly illumination or observation angle dependent reflection properties. A description of effect color layers is found, for example, in the articles "Pigments—Coloring Agents and Functional Carriers" of C.D. Eschenbach and "Pearlescent Pigments" of G. Pfaff in Spektrum Der Wissenschaft, October 1997, pgs. 94–99 and pgs. 99–104. Such angle dependent special effects can at this point in time not be captured within a color management system.

A strongly angle-dependent surface gloss also occurs with printed metallically glossy substrate materials or foils, which must be captured by measurement technology for a correct reproduction.

For the application as a built in sensor, a measurement system must fulfill the following basic requirements: it must permit fast measurement cycles, have a compact construction and low weight, must be robust and have a long service period, and must be as maintenance free as possible. Furthermore, a measurement system must enable a contact free measurement geometry to the sample in order to be used in online or inline operation in an automated system. For color management applications in the graphics area, color measurement devices with 45E/0E or 0E/45E measurement geometry are currently used, which are realized in compact construction. A typical example is the spectrophotometer "Spectrolino" of the company Gretag-Macbeth AG and the reference EP-A 1067369. The measurement technology used is based on an incandescent lamp as illumination source and a diode array—grating—spectrometer for the spectral evaluation in the measurement channel. The "Spectrolino" spectrophotometer can be added as a measurement head onto an xy—displacement table, for example, the "SpectroScan" type of the company GretagMacbeth AG, which allows for the automated measurement of a large number of color samples possible for the generation of a printer device profile.

The measurement technology used in the "Spectrolino" is not suitable for use as a built-in sensor for various reasons. The incandescent lamp has a finite service life. The measurement system must therefore be designed especially for an easy lamp replacement. The filament of the incandescent lamp is sensitive to vibrations, which creates difficulties upon installation into motorized systems. The measurement system is also sensitive to variations in the distance between the sample and the measurement optics. As a consequence, the measurement in these apparatus is carried out in direct mechanical contact with the sample.

The use of a color measurement device with 45E/0E measurement geometry in digital printing systems for color management applications is described, for example, in DE-C 197 22073.

Angle dependent reflection properties cannot be captured with the 45E/0E geometry. Known processes of this geometry can include the use of additional optical filters which can be moved into the elimination and measurement channel for the evaluation of material parameters, such as surface effect and fluorescence excitation of optical brighteners. For the elimination of the surface effect, a measurement with crossed linear polarization filters can be used and light type conversion filters can be used for the fluorescence excitation. For automatic measurement systems, this functionality must be achieved with mechanically operated components, for example, with a filter wheel as realized in the spectrophotometer "Spectral Eye" of the company Gretag-Macbeth AG. Moveable mechanical components are not suitable for compact sensor systems.

Alternative technologies in combined measurement devices for color and surface properties are based on a diffuse measurement geometry with an Ulbricht Sphere or the use of a gloss measurement.

A gloss trap can be incorporated in the Ulbricht Sphere in the diffuse measurement geometry, which eliminates oriented light reflected from the probe surface in the measurement channel. An advantageous embodiment of this measurement principle is described, for example, in EP-A 0964244. However, the diffuse measurement geometry must by definition be realized in direct contact with the sample to be measured. The measurement geometry with the Ulbricht Sphere is not suited for miniaturization and the manufacture of a well reflecting Ulbricht Sphere is costly. Furthermore, the geometry of the Ulbricht Sphere is not directly applicable for the fluorescence measurement and must be especially calibrated.

In gloss measurement devices, the sample is directionally illuminated with a narrow band light source and the portion of the light directionally reflected by the surface is measured with a detector. A degree of gloss which is characteristic for the surface is determined from the measured value. This degree of gloss represents the surface quality, but not directly the visual color perception and is therefore not suited for visualization applications in the color management field. Combined color measurement devices with 45E/0E measurement geometry and integrated gloss measurement are described in U.S. Pat. No. 5,377,000 and U.S. Pat. No. 4,886,355. A commercial product with this functionality is available from the company BYK-Gardener under the name "Color—Guide Gloss".

Different manufacturers offer multi-angle spectrophotometers for color measurement technology. Typical examples herefor are the apparatus with product designation "MA68IL" available from the company X-rite, Inc. (Grandville, Mich., USA), product designation "CM512m3" available from the company Minolta Co., Ltd. (Osaka, Japan), as well as product designations "CE640" and "CE740" available from the company GretagMacbeth AG (Regensdorf, Switzerland). Although some of these apparatus are portable, they have a complex mechanical construction and must be mechanically placed onto the sample for measurement. These systems also cannot be used as built-in sensors because of their size.

SUMMARY OF THE INVENTION

Starting from the state of the art, it is now an object of the present invention to provide a spectrophotometer which is especially adapted for color management applications.

It is a further object to provide a spectrophotometer which fulfills the above-mentioned basic requirements and enables, while being of compact construction, a versatile use for all input and output media involved in a color management system.

It is another object of the invention to provide a spectrophotometer which can be used especially as a built-in device or measurement sensor in automated color measurement systems or directly in color printing systems.

Preferably, the spectrophotometer in accordance with the invention is suitable for the measurement of color, as well as material and color reproduction properties, and effect color layers, and allows the formation of device profiles of the most different type from the measurement results to thereby enable an exact visualization of the color reproduction properties of a manufacturing process.

The solution of these objects is provided by the spectrophotometer in accordance with the invention, whereby the measurement head has an illumination channel for each light emitting diode so that the light originating from each light emitting diode is directed under a defined angle of incidence onto the measurement spot of the sample, the electronic circuitry is adapted for the selective control of the light emitting diodes forming the illumination source, and the illumination light source includes at least one white light emitting diode.

In a preferred embodiment, the invention provides a Spectrophotometer for the measurement of light remitted or emitted from a sample to be measured, including a measurement head, an illumination arrangement for the sample to be measured and housed in the measurement head, the illumination arrangement having an illumination light source essentially continuous in the visible spectral range and formed by light emitting diodes, the illumination light source including at least one white light emitting diode, a collecting arrangement also housed in the measurement head for the capturing of measurement light originating from a measurement spot on the sample, a spectrometer optically connected to the collecting arrangement for the splitting of the measurement light captured by the collecting arrangement into its spectral components and for the generation of corresponding electrical measurement signals, and an electronic circuit for the control of the illumination arrangement and the spectrometer as well as for the processing of the electrical measurement signals, the measurement head including an illumination channel for each light emitting diode for directing the light originating from each light emitting diode at a defined angle of incidence onto the measurement spot on the sample and the electronic circuit being constructed for selectively controlling the light emitting diodes forming the illumination light source.

BRIEF DESCRIPTION OF THE DRAWINGS

The invention will now be further described by way of example only and with reference to the attached drawings, wherein.

DETAILED DESCRIPTION OF THE PREFERRED EMBODIMENTS

Figure 1:
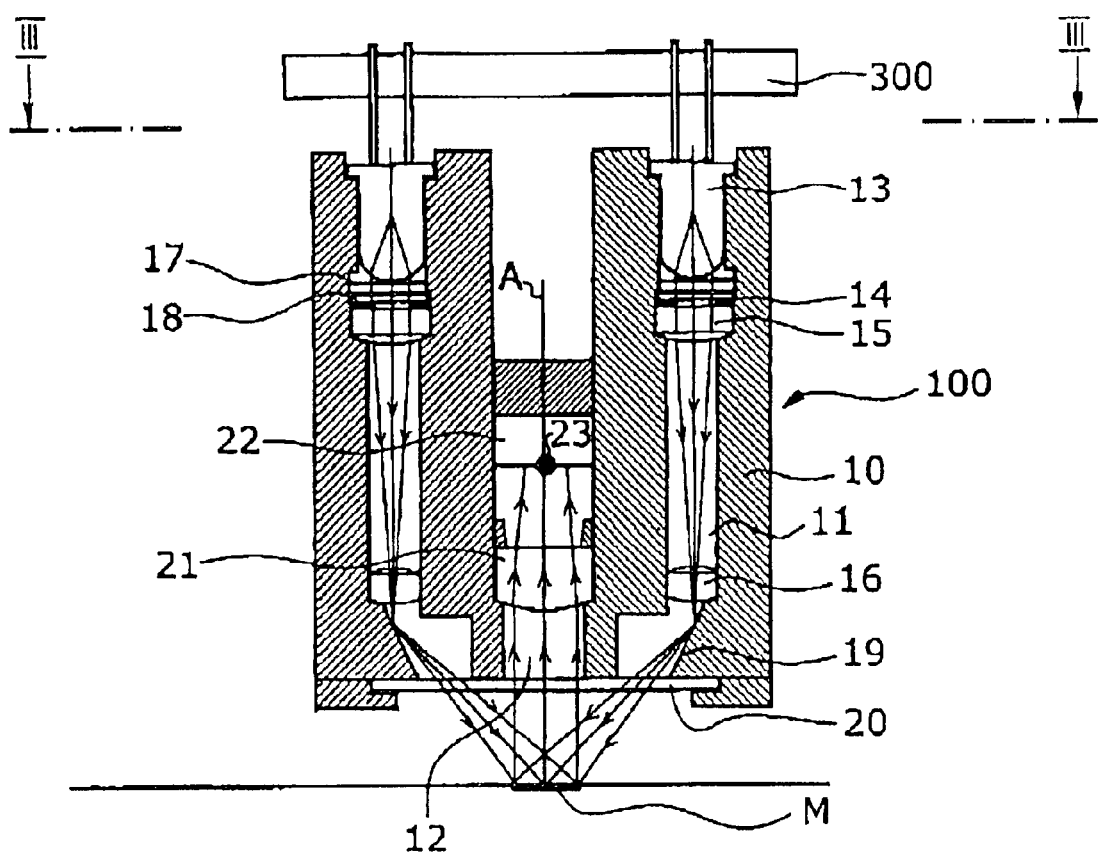
FIG. 1 illustrates an axial section through a first preferred embodiment of the spectrophotometer in accordance with the invention, taken along line I—I in FIG. 3.
Figure 2:
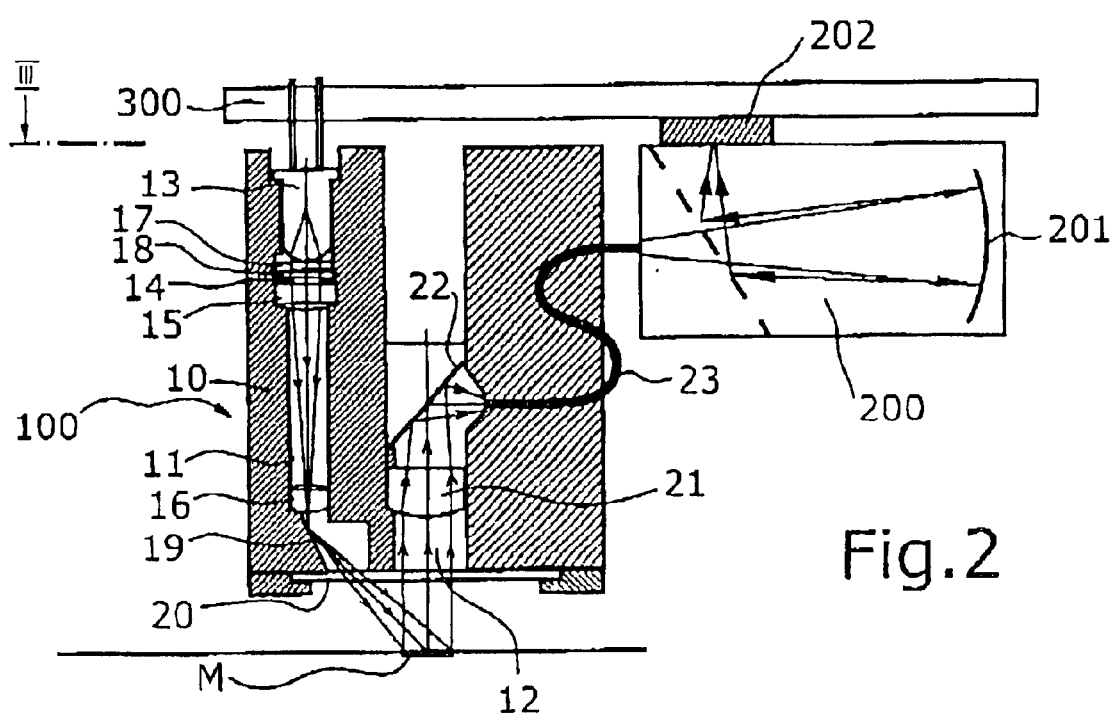
FIG. 2 is an axial section taken along line II—II in FIG. 3.
Figure 3:
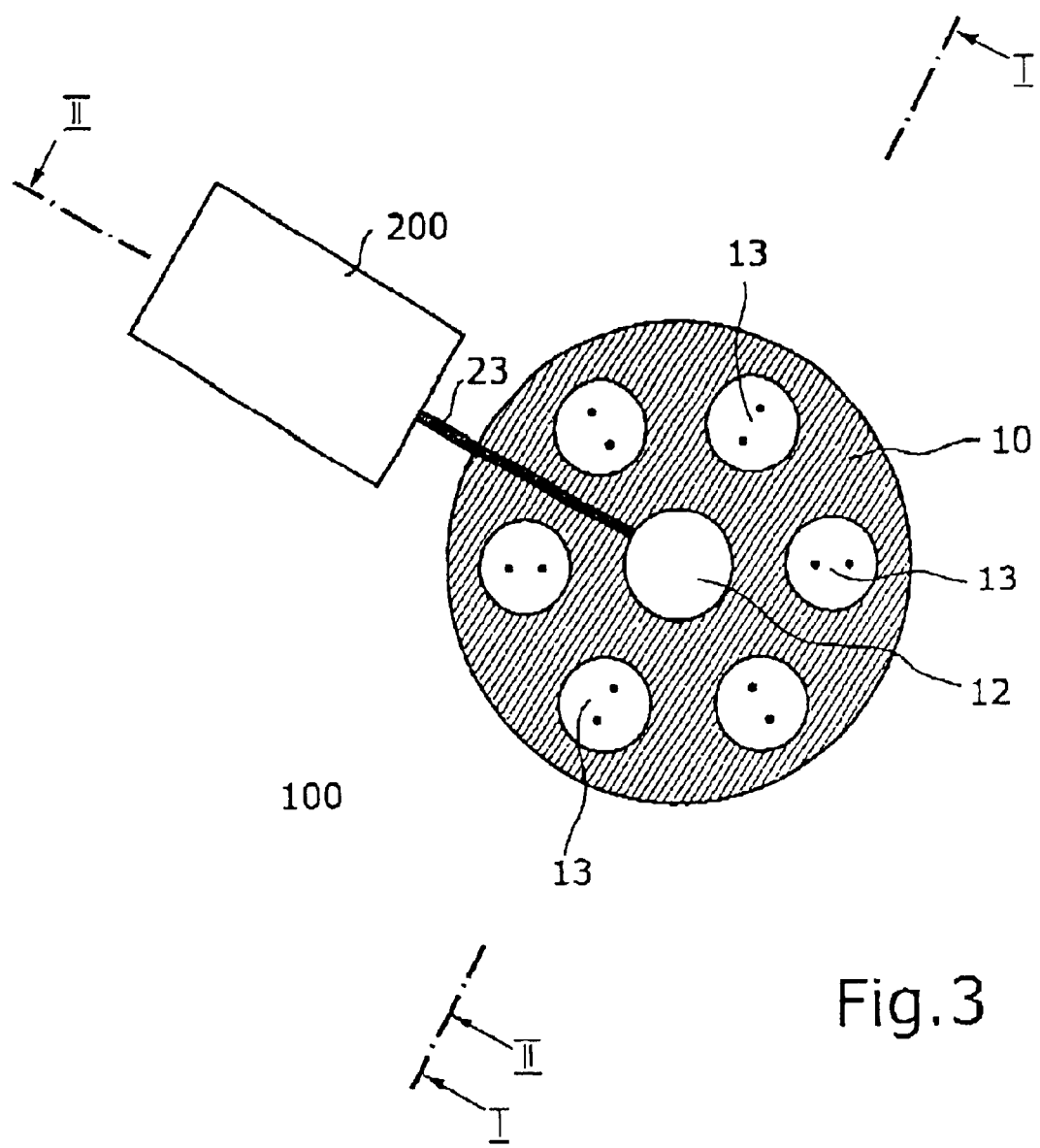
FIG. 3 is a cross-section through the embodiment shown in FIG. 1 taken along line III—III in FIG. 1.

The principle construction of a first embodiment of the spectrophotometer in accordance with the invention and adapted to a 45E/0E measurement geometry is illustrated in FIGS. 1 to 3. The spectrophotometer as shown includes an illumination arrangement with a spectrally essentially continuous illumination light source including multiple individual light sources and optical means to separately direct the light originating from the individual light sources onto the sample to be measured, a collector arrangement for the capturing of the measurement light originating from the measurement spot on the sample, a spectrometer (spectral analyzer) for the splitting of the captured measurement light into its spectral components, and an electronic circuit for the control and signal processing.

In particular, the spectrophotometer includes an optical measurement head 100, a spectrometer 200 and a circuit board 300, which mechanically and electrically connects the measurement head and the spectrometer and includes the total electronic circuit for the control of the measurement head and the spectrometer.

The measurement head 100 includes an outwardly essentially cylindrical housing 10, in which continuous illumination channels 11 are positioned in a circle evenly distributed about the optical axis 8, in this example 6 channels. Furthermore, a collector channel 12 is axially provided in the measurement head 100 which (in this Figure) is downwardly open. The 6 illumination channels 11 and the collector channel 12 are at their (in this Figure) lower end covered by a transparent disk 20 and thereby protected from dirt. The housing 10 of the measurement head 100 is constructed in such a way that the disk 20 is easily reachable and can be cleaned. The collector channel 12 is thereby preferably telecentrically constructed, which means the same angle is measured from each point in the measurement field.

A light source 13 constructed as a light emitting diode (LED), which is electrically mounted on the circuit board 300, is provided in each illumination channel 11 at the upper end (in this Figure). Furthermore, a field shutter 14, a condenser lens 15, an imaging lens 16, a diffraction disk 17, one or more filters 18 and a redirecting mirror 19 are located in each illumination channel 11. The mentioned optical components 13–19 are dimensioned and positioned in such a way that each LED-light source 13 illuminates a coaxial measurement spot M of the object to be measured located below the measurement head 100 at an illumination angle of essentially 45E. The diffraction disks 17 and/or the filters 18 can also be omitted, depending on the type of the light emitting diodes 13 used, or depending on the specific purpose of the spectrophotometer. The light sources 13 implemented as LED's (here 6) together form a spectrally essentially continuous illumination light source.

A collector lens 21 and a redirecting mirror 22 are found in the collector channel 12. These two components collect the measurement light remitted or emitted from the measurement spot M at an angle of observation of essentially 0° and couple it into an optical fiber 23 protruding laterally from the measurement head. The fiber guides the captured measurement light into the spectrometer 200, where it is divided into its spectral components in a known manner. The spectrometer may be advantageously constructed according to EP-A 1041 372 and includes a dispersing optical element, a diffraction grating 201, and a diode array 202 as light sensor, whereby the latter is preferably positioned such that it is mounted directly on the circuit board 300 (FIG. 3). Alternative spectrometer designs may be employed according to present invention. The diode array 202 produces in a known manner electrical signals which correspond to the spectral components of the received measurement light.

The measurement principle used in the spectrophotometer in accordance with the invention is based on the generally known concept of a (spectrally) continuous light source and a collecting channel with a connected spectral analyzer (spectrometer). This measurement principle enables at the same time high spectral resolution and short measurement cycles. This measurement principle can be used in a manner known in the art at the same time for remission measurements with an illumination positioned in the measurement head and for emission measurements at auto luminous bodies.

According to an essential aspect of the invention, white semiconductor luminescence diodes (LED) 13 which radiate over the whole visible spectral range are used for the realization of the continuous light source. Such white LEDs have lately become commercially available from different manufacturers. These LEDs produce the white continuous illumination spectrum by way of luminescence conversion. They are made of an LED chip which emits light in the blue, violet or UV spectral range. In addition, fluorescent pigment layers are used in the LED housing, which are optically excited by the light emitted by the LED chip and reemit light of a larger wave length. The construction and the functioning of white luminescence LEDs is described, for example, in the publication "White Light Emitting Diodes" by J. Bauer, P. Schlotter, and J. Schneider in R. Helbig (Ed.) Solid Body Problems, Vol. 37, Braunschweig: Vieweg, 1998, Pgs 67–78.

Compared to incandescent or flash lamps, white LEDs provide fundamental advantages in spectrophotometers.

LEDs have a long service life of typically 50,000 hours, so that the measurement system can be built simply without exchangeable illumination unit. White LEDs produce a spectrum limited to the visible spectral range. For that reason, no additional band limiting filters need to be included in the collector channel for a spectral measurement with a grating spectrometer. LEDs have a good efficiency so that they can be operated at a lower electrical power and produce little heat. Furthermore, LEDs can be operated in short pulses.

These facts enable the realization of novel compact multifunction illumination lens systems for spectro-photometric sensor systems. Because of the low level of heat generation, several LED chips can be installed within a small space in enclosed housings. The combination of several light sources enables high light intensities in the measurement field. Furthermore, multi-channel illumination systems can be realized with several LEDs.

Because of the low heat generation, LEDs are also ideal light sources for combination with a plastics lens system. Optical components of plastics can be placed in the immediate vicinity of the light source or even rigidly connected with the light source. This allows for a compact construction, low weight and low manufacturing cost. Additionally, mechanical positioning aids for the LED light sources can be integrated directly into the plastics components. This allows for a simple installation during manufacture without active adjustment of the light source relative to the illumination lens system.

It is possible to assign to the combination of sensor and LED, or sensor and LEDs both a separate and common lens systems, whereby the latter solution is more cost efficient.

In the advantageous embodiment of FIGS. 1–3, the electronic circuit and the LED light sources are installed on a common circuit board 300. The LEDs are installed in standard housings. In order to achieve high light intensities in the measurement field M, the illumination is formed of several LED light sources, which are arranged in the measurement head 100 or on the circuit board 300 in a circle and concentrical with the collecting channel 12.

Mechanical positioning structures for the LED light source are provided in the illumination channels 11 in the housing 10 of the measurement head 100, so that the LEDs can be easily inserted during the installation and need no longer be adjusted.

The illumination system realizes for each LED 13 a two-step imaging system. The light of each individual LED 13 is first guided through the (optional) filter 18. This filter 18 serves to optimally adapt the emission spectrum of the LED to the desired application, for example, to achieve a constant electrical measurement signal over the spectral measurement range. The diffraction disc 17 positioned in the light path after the LED light source 13 angularly mixes the light beams, since the emission characteristic of a white LED is spectrally not constant.

The field stop 14 limits the three-dimensional extent of the illumination spot in the measurement field M. The first condenser lens 15 captures the light of the light source 13 and creates an intermediate image of the light source. A second imaging system consisting of a combination of imaging lens 16 and redirecting mirror 19 then creates a limited illumination spot in the measurement field M under a specific angle of incidence (here 45°).

In an advantageous embodiment, the optical components in the illumination system (condenser lens 15, imaging lens 16) are formed of integral, annular plastics components, as further explained in connection with FIG. 5, which integrate at the same time all lenses of the individual illumination channels. This reduces manufacturing cost and simplifies installation.

In the embodiment according to FIGS. 1–3, the collector lens 21 focuses the light onto the optical light conducting fiber 23, which is positioned in the focal point of the collector lens 21. The optical fiber guides the measurement light to the spectrometer 200. The coupling into the spectrometer 200 can also be realized directly by way of an entry slit without optical fiber. In an especially advantageous embodiment, the spectrometer is realized as a plastic diode array grating spectrometer as in EP-A 10141372.

Figure 7:
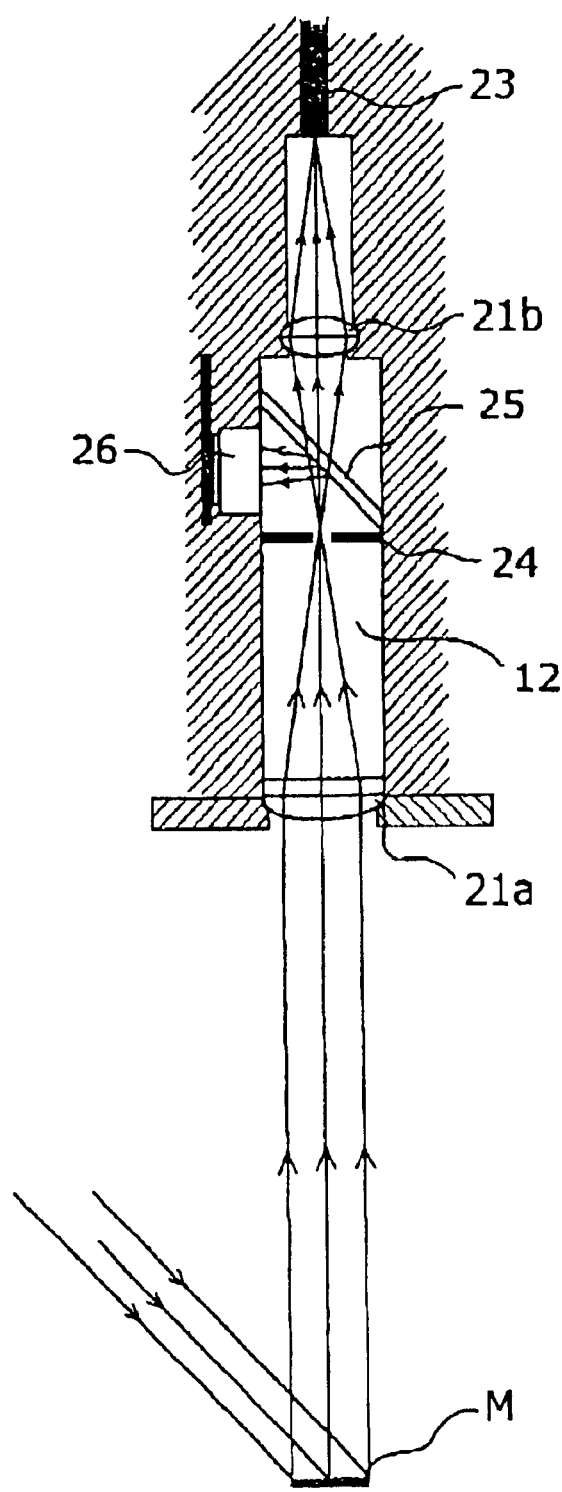
FIG. 7 is a principal schematic for the illustration of a first variant of an integrated distance measurement.

In order to achieve a large depth of focus, the collecting channel is preferably constructed as a telecentrical imaging system (see FIG. 7). The measurement field is thereby imaged in focus by a first lens 21a in telecentrical positioning. A diaphragm 24 is positioned in the image plane which sharply limits the measurement field. A second lens system 21b then couples the light into the spectrometer. The coupling into the spectrometer can thereby also be realized directly by way of an entry slit or by way of an optical fiber 23.

Figure 4:
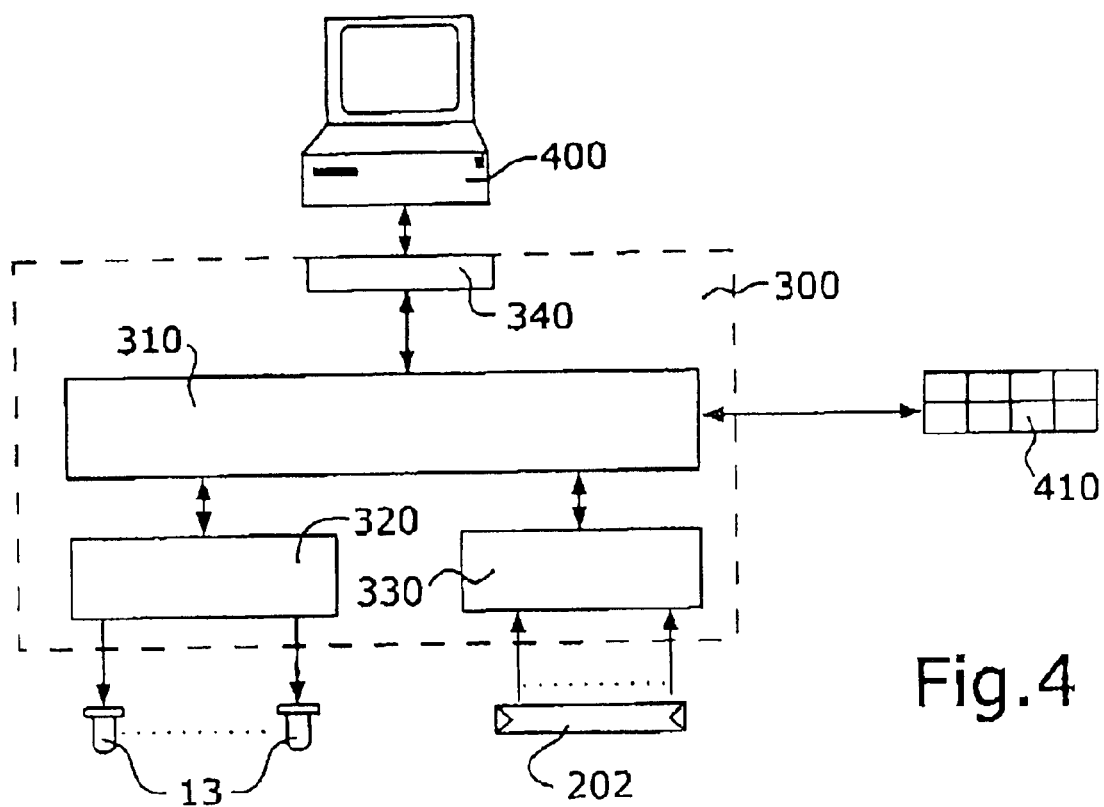
FIG. 4 is a principle schematic of the electronic components of the spectrophotometer in accordance with the invention.

The electronic circuit on the circuit board 300 includes, as shown in FIG. 4, a processor supported control 310, a driver stage 320 for the selective control of all LED light sources 13, a driver stage 330 for the control of the diode array arrangement 202, and an interface 340 for the communication with an external computer 400. Operating members (for example keys) 410 are optionally provided for the communication with the control 310. The electronic circuit of the spectrophotometer is so far of essentially conventional construction and controls in an also known manner the measurement process, whereby the determined measurement data are communicated to the external computer by way of the interface 340. The external computer can as is generally known also control the measurement process. The electronic circuit controls especially also the operation of the LED light sources 13. The light emission of the LEDs 13 is controlled according to known processes, for example, as described in the book "Optoelectronics/Fiberoptics Applications Manual" $2^{nd}$ Edition of the Hewlett-Packard Company, Optoelectronics Division, Applications Engineering Staff, 1981, Pages 2.1 to 2.55.

The above-described spectrophotometer in accordance with the invention can be further expanded in that not only white LEDs, but also LEDs of other colors are employed as light sources 13. This enables the realization of different, especially advantageous further developments or variants of the spectrophotometer, as described in the following.

The first further development concerns the realization of an electronically switchable UV light source. This light source is realized in that several white LEDs and additionally WV LEDs are installed as light sources 13. WV LEDs emit mainly light in the ultraviolet spectral range between 350 nm and 420 nm. The electronic operation and control of the LED light source is thereby constructed in such a way that the emitted intensity of each individual LED 13 can be adjusted individually (or in groups). The percentage proportion of the WV light compared to the visible light spectrum can thereby be varied in the overlapped, total illumination spectrum. This process enables a variable, electronically controllable fluorescence excitation of optical brighteners in the sample to be measured. This variant corresponds to an electronically controllable UV filter in the illumination lens system, whereby however no mechanically movable components are required. Especially, defined light types (for example the standard light types defined by the CIE) or real light sources with different UV proportion can be simulated in the measurement head, which enables the measurement of color data with correct fluorescence evaluation of optical brighteners. The consideration of real illumination sources in the color measurement technology results in a large advantage for digital visualization and test applications in the color management field.

A further variant of the spectrophotometer in accordance with the invention includes the realization of an additional also precisely spectrally measuring density measuring head. For this additional functionality, (at least) 3 colored LEDs are employed in addition to the white LEDs, which emit only in the red, green or blue spectral range.

In the density measurement with a (conventional) spectrophotometer with continuous white illumination spectrum, the scattered light produced in the spectral analyzer by the broadband illumination limits the usable density measurement range. This can be avoided with the spectrophotometer optimized according to the invention, in that the density measurement is carried out in 3 sequential measurements, whereby in the individual measurements only the red, green or blue LEDs are switched on. The illumination spectrum is thereby effectively limited to the corresponding density measurement range. This reduces the scattered light level and increases the linear measurement range of the spectrophotometer. Since the measurement is carried out spectrally, the emission spectrum of the individual LEDs need not be adjusted to the desired exact density filter function. The desired density filter characteristic is realized in a known manner by way of a processor. The electronic circuit 310-340 can therefor include different pre-defined density filter functions as spectral data tables, on the basis of which it calculates the desired density values from the spectral measurement signals. The digital filtering or calculation of the density values can of course also be carried out by way of an application program which runs on the external computer connected to the densitometer.

For the application as a pure densitometer, the white light source can of course be obviated. Significant advantages may be realized by utilizing the disclosed construction, features and/or functionalities in the manufacture of densitometers, and such densitometer constructions (and applications thereof) are claimed herein.

A continuous illumination spectrum over the visible and ultraviolet spectral range can also be achieved by a combination of several narrow band emitting LEDs. LEDs have typical spectral half value widths of 20–50 nm. Therefore, about 8 different LEDs must be used in a common annular illumination analogous to FIGS. 1–3 for a continuous spectrum over the visible range of 400–700 nm. If no narrow band LEDs can be found in a certain spectral range, broadband LEDs in combination with corresponding filters can be used.

For this further development, the illumination spectrum in the spectrophotometer can be adapted to a desired theoretical or measured illumination distribution over the whole spectral measurement range. This electronically adjustable light source enables the correct color evaluation for generally fluorescent colors. The measurement process can be carried out with a single measurement with all LEDs switched on.

This further development of the spectrophotometer also makes the realization of a simple compact double monochromator-spectrophotometer possible. In this application, a spectral measurement is sequentially carried out for each independent spectral range of the light source formed by the different LEDs by corresponding control of the LEDs. These multiple measurements enable the lowest scattered light levels possible and a commonly applicable evaluation of fluorescence effects.

The color measurement of effect color layers must be carried out with a multi-angle measurement geometry. The control and the description of the angle dependent color behavior of effect color layers requires the measurement with at least 3 characteristic (illumination) angles, which are specified, for example, in the standards ASTM E284 (15°, 45°, 110°) and DIN 6175-2 (25°, 45°, 75°).

Figure 5:
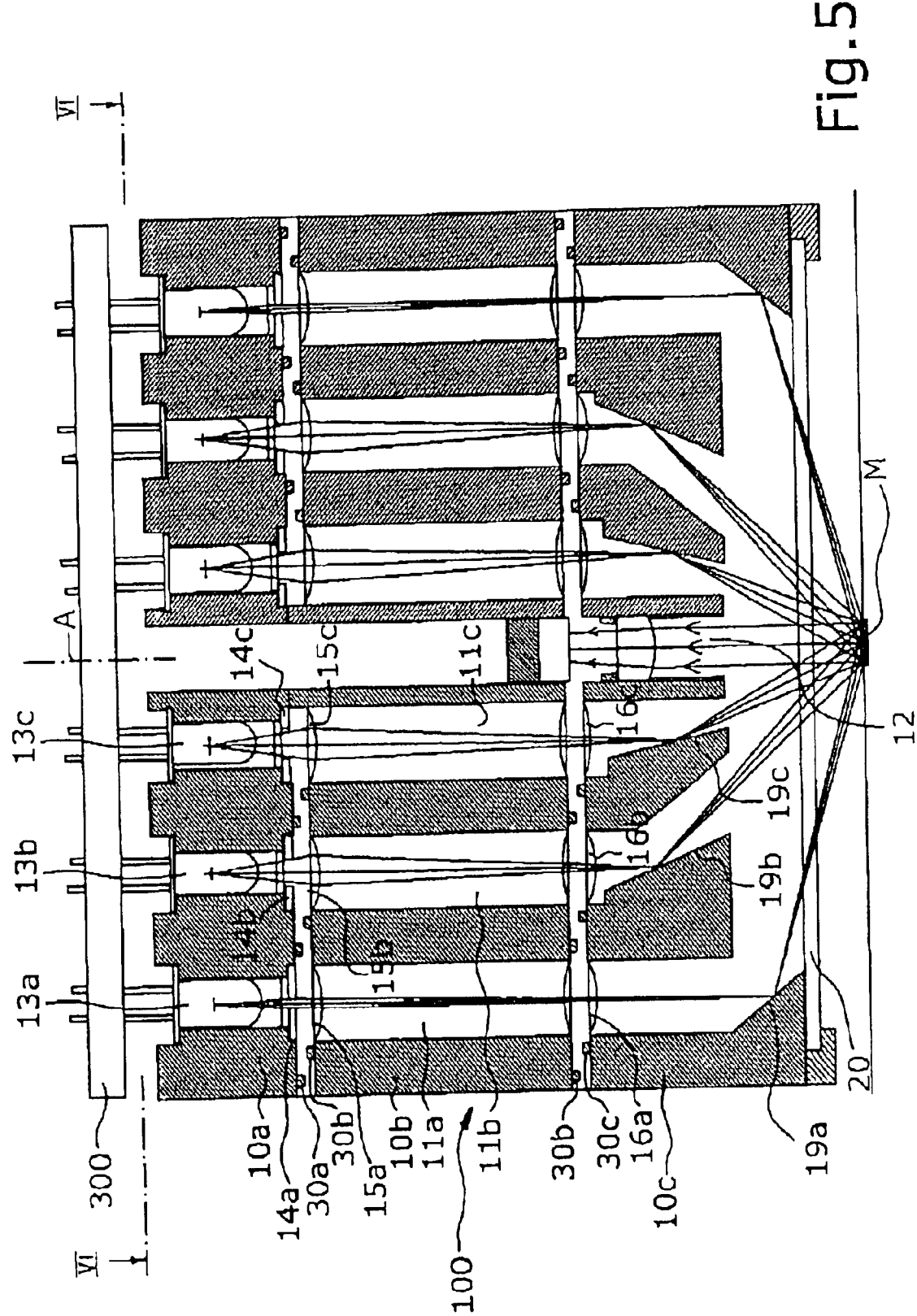
FIG. 5 is an axial section analog to FIG. 1 through a second preferred embodiment of the spectrophotometer in accordance with the invention.
Figure 6:
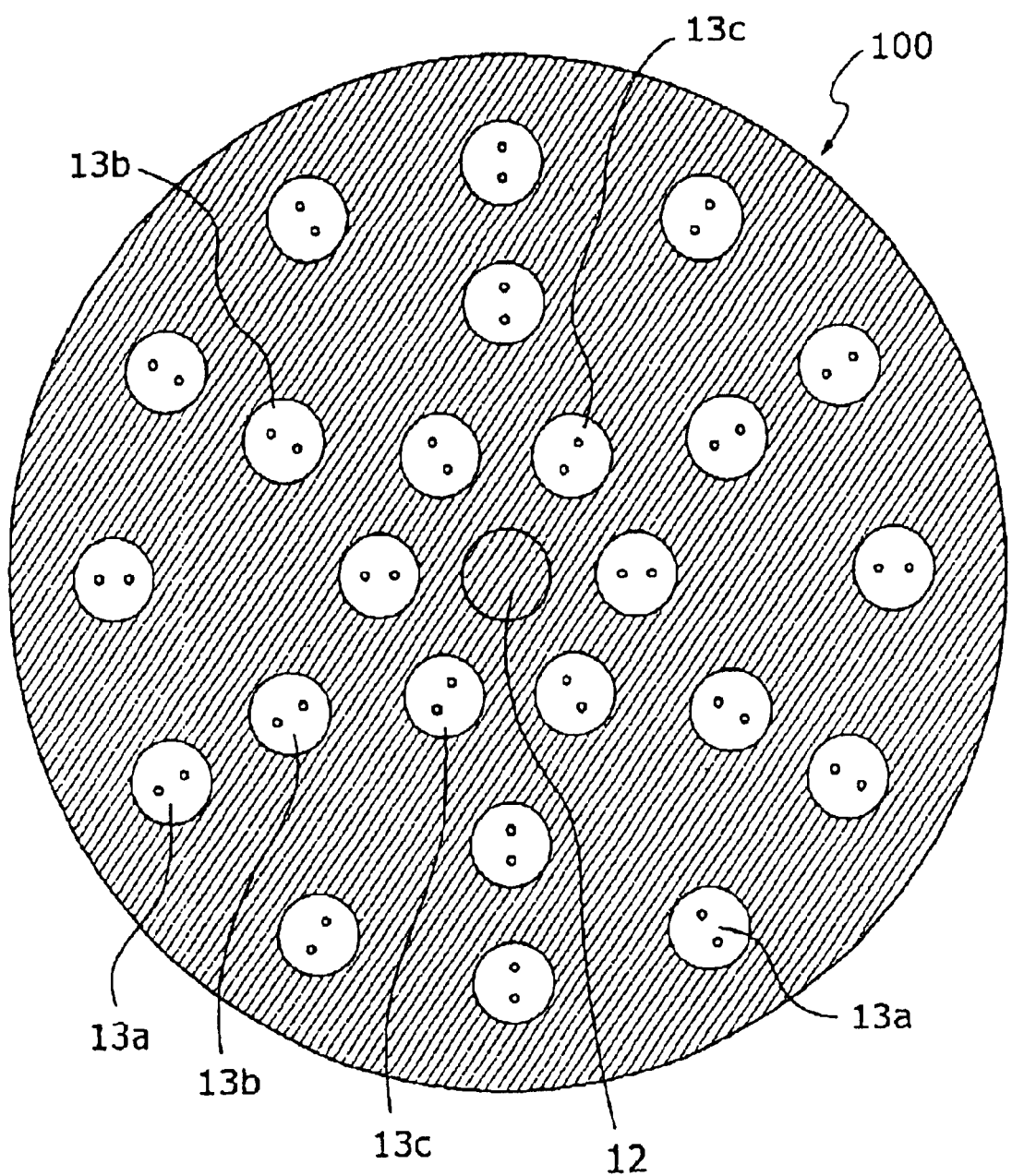
FIG. 6 is a cross-section through the embodiment of FIG. 5 and analog to FIG. 3 but taken along line IV—IV in FIG. 5.

A second embodiment of the spectrophotometer in accordance with the invention is schematically depicted in FIGS. 5 and 6, which is adapted for multi angle measurements (in this example 25°, 45° and 75°).

The measurement head 100 is principally constructed the same as that of the embodiment of FIGS. 1–3, but includes not only one, but three concentrical, annular arrangements of illumination channels which are labeled 11a, 11b, and 11c. Each illumination channel in turn includes an LED light source, a diffraction disk (optional), a filter (optional), a field stop, a condenser lens, an imaging lens and a redirecting mirror, whereby the parts of the illumination channels corresponding to those in FIG. 1 are labeled with the same reference numbers, but corresponding to their association with one of the three annular arrangements of illumination channels 11a, 11b, 11c, are labeled with additional indices a, b and c. All remaining parts of the spectrophotometer are constructed the same as or analogous to those of the embodiment of FIGS. 1–4.

In each circular arrangement of illumination channels 11a, 11b, 11c, the light of at least one white LED and possibly still additional LEDs (single color, UV) is coupled in, and directed at a defined angle (in this example 25°, 45° and 75°) onto the measurement field. The geometry of each annular arrangement can be variable, which means each "annular" arrangement can include a different number of illumination channels. Accordingly, for each illumination angle (relative to the optical axis A) light falls onto the sample from one or more (radial) directions. The measurement geometry is such that no optical cross-talk between the channels with different illumination angle can occur, including the associated LED light sources.

As in the example of FIGS. 1–3, each LED light source is imaged into the common measurement field M with a two step imaging system consisting of a condenser lens and an imaging lens. The optical imaging system further includes the field stop, which defines the size of the illumination spot in the measurement field, and possibly additional filters and the diffraction disk. The illumination angle onto the measurement field is defined in each illumination channel by the redirecting mirror. The diameter of the field stop of each illumination channel must be adapted corresponding to the cosine of the illumination angle in order to illuminate an equal size measurement field. This requires small stop openings at large illumination angles and means a light loss. This light loss can be compensated by the use of a larger number of LEDs in the respective illumination channels.

The advantageous embodiment of FIGS. 5–6 enables the positioning of all LED light sources at the same height above the measurement field. This enables a simple installation of all LEDs in standard housings on the common circuit board 300.

Furthermore, the two lenses (condenser lens and imaging lens) are realized in all illumination channels at the same height above the measurement field. It is required herefor that the focal lengths of the two lenses are coordinated in each illumination channel to the respective mutual positions of the illumination channels.

This special arrangement offers fundamental advantages for the manufacture of the spectrophotometer. The normally difficult adjustment of a multi channel illumination system such that the light of all illumination channels cleanly falls into the common measurement field can be easily solved with this arrangement.

The condenser lenses and the imaging lenses of all illumination channels are therefor, as is shown in FIG. 5, realized as physically integrated (one piece) lens arrays. This reduces the manufacturing cost, since only one component must be manufactured, for example from plastic in an injection molding process. Furthermore, an exact mutual positioning of the lenses is achieved by the integration into one element. Additionally, mechanical positioning structures (in the form of recesses) are integrated into the lens arrays, which cooperate with corresponding position structures (for example in the form of projections or pins) in the measurement head housing and thereby allow for an adjustment free assembly of the measurement head.

The housing of the measurement head 100 consists essentially of three parts 10a, 10b, 10c, which are provided with pin-shaped positioning structures 30a, 30b, 30c.

An upper housing portion 10a includes the mounts for the LED light sources and is pinned by way of the positioning structures 30a onto the condenser lens array 15a–15c.

A middle portion 10b serves as spacer to the lens array of the collector lenses 16a–16c. It is provided with the positioning structures 30b and by way of the latter connected with the two lens arrays 15a–15c and 16a–16c.

A lower housing portion provided with the positioning structures 30c includes the redirecting mirrors 19a–19c and is by way of the positioning structures fastened to the imaging lens array 16a–16c and oriented in relation thereto.

The LED light sources are operated in short pulses for the measurement process so that temporally sequentially only the LEDs belonging to respectively one illumination angle are activated and the respective reflection spectrum under the respective illumination angle is detected.

The illumination system of the measurement head is constructed such that at least one illumination channel illuminates the measurement field at an angle of 45°. Ideally, illumination angles corresponding to the standards for multi angle color measurement devices (for example ASTM E 284 and DIN 6175–2) are implemented for additional illumination channels.

For the application of the spectrophotometer in a printing or automated color management system, a contact free measurement geometry must be realized between the measurement head and the sample. The 45°/0° and multi angle measurement geometries are very sensitive to changes in distance, because of the large illumination angles. In known systems, for example according to U.S. Pat. No. 6,198,536, a complex mechanical construction is provided which ensures a constant measurement distance during the measurement process. Such constructions are costly and not generally applicable for built in sensors.

According to a further aspect of the invention, an optical distance measurement integrated in the measurement head, and a numeric correction of the measured data for compensation of the influence of distance measurements during the measurement process are now used. Significantly higher thresholds for tolerable distance variations are achieved, so that a simpler mechanical construction can be used for the installation of the sensor.

A first variant of a distance measurement integrated with the measurement head is schematically illustrated in FIG. 7.

The optical distance measurement is based on a trigonometric measurement process. A change in the measurement distance due to the large illumination angle causes a lateral displacement of the illumination spot relative to the measurement field of the collector channel. This lateral displacement creates a change in the signal level and leads to measurement errors. The lateral displacement of the illumination spot is measured and analyzed for the numerical correction.

The collector channel 12 is constructed to enable an imaging of the measurement field onto an optical sensor 26. In the preferred embodiment according to FIG. 7, a telecentrical imaging system is provided in the collector channel 12 on the measurement field side. A first lens 21a creates an intermediate image in the collector channel. A diaphragm 24 is positioned in the focal point of the first lens 21a and limits the capture angle of the measurement field. After the diaphragm 24, the optical light path is divided by way of a beam splitter 25. The large portion of the measurement light is coupled into the optical fiber 23 by way of the second lens 21b, guided in the latter to the spectrometer 200 (FIG. 2). A smaller portion is used to be able to measure the lateral displacement by way of the optical sensor 26 positioned in the image plane of the measurement field. The optical sensor 26 can, for example, be constructed as a two-dimensional image sensor (CCD chip), as a position sensitive detector (PSD) or as a 4-quadrant detector, whereby the determination of the lateral displacement is carried out by way of the sensor 26 by generally known methods.

During the manufacture and calibration of the measurement head or the spectrophotometer, the relative signal changes corresponding to certain displacement values are measured and stored. The correction factors for the measurement values are determined therefrom during the measurement operation. This can be carried out by way of numerical interpolation between the stored values. The correction of the measured data need not be carried out in the spectrophotometer itself. It can also be carried out in an external computer, which only gets transmitted the measurement values from the spectrophotometer.

Figure 8:
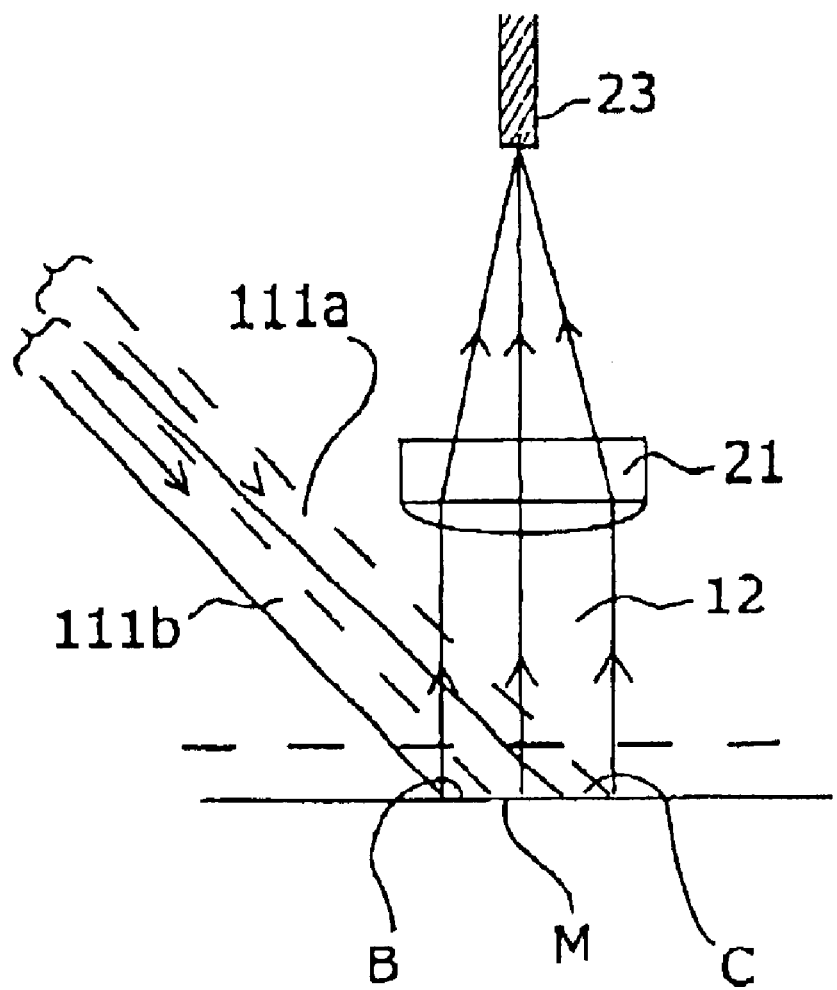
FIGS. 8 and 9 are two principal schematics for the illustration of a second variant of an integrated distance measurement.
Figure 9:
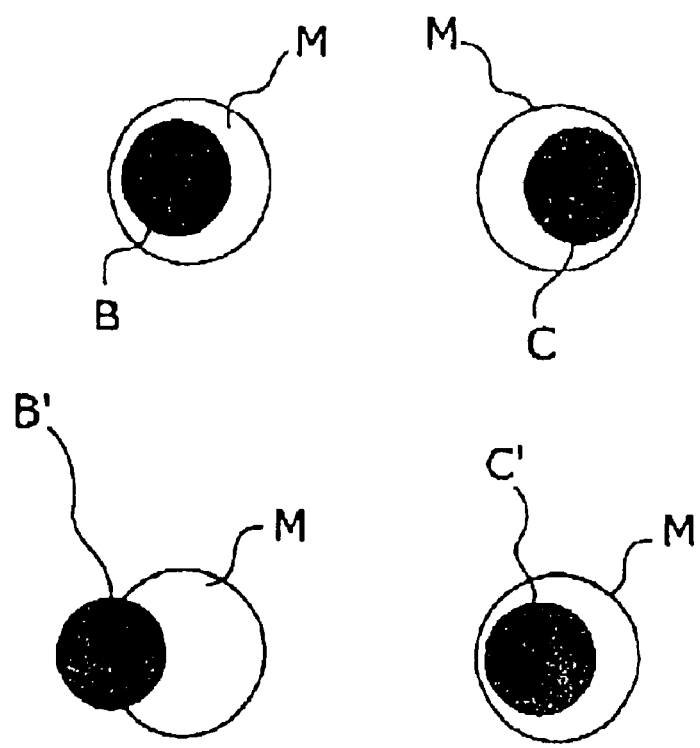

An alternative implementation of the distance measurement principle is made possible by the installation of two illumination channels 111a and 111b, which illuminate the measurement field at the same angle, but produce two laterally offset illumination spots. This variant is schematically illustrated in FIGS. 8–9. M therein refers to the measurement spot captured by the collector channel 12 on the sample to be measured, B and C or B' and C' refer to the illumination spots produced by the two illumination channels 111a and 111b at two different distances.

Upon distance changes, the two illumination spots B and C shift relative to the measurement field M. Because of the lateral displacement, a different signal change is achieved upon the measurement of each individual illumination channel with the spectral collector channel. The ratio of these two measurement signals is a characteristic parameter for the distance change. This ratio can be measured as a function of the distance change during calibration of the spectrophotometer and assigned to a corresponding signal level correction. This second realization has the advantage that the same optical components are used for the color and distance measurement.

The use of the multi angle embodiment of the spectrophotometer in color management applications enables the visualization and simulation of angle dependent color and reflection properties of a specific reproduction process. For this application, according to the principles of the color management, a color chart which represents the color space of a printing system well, is spectrally measured with the multi angle spectrophotometer in accordance with the invention. The remission spectra of each illumination angle are stored for each measurement field. Using a specified observer and an illumination spectrum, the remission spectra can be recalculated into color values (CIE, XYZ or L*a*b) according to known processes.

Multi angle device color profiles are produced from the multi angle color measurement data and the associated system control signals of the target device (for example a printer). For an easy use in standard color management systems, a device profile according to the ICC definition is created for each measurement angle. This device profile corresponds to a table, which assigns to the measured system control signals the corresponding color values. Missing color values are determined by interpolation between measured values in the table. These multiple profiles can be loaded in and used in an ICC compatible image processing software, for example PHOTOSHOP from Adobe, in order to reproduce on the screen the angle dependent color properties of a digital image or document, which is produced according to a specific printing process.

It will be appreciated by those skilled in the art that the present invention can be embodied in other specific forms without departing from the spirit or essential characteristics thereof. The presently disclosed embodiments are therefore considered in all respects to be illustrative and not restrictive of the scope of the present invention. The scope of the presently claimed invention is indicated by the appended claims, rather than the foregoing description and all changes that come within the meaning and range of equivalents thereof are intended to be embraced therein.

What is claimed is:

1. Spectrophotometer for the measurement of light remitted or emitted from a sample to be measured, comprising a measurement head, an illumination arrangement for the sample to be measured and housed in the measurement head, the illumination arrangement having an illumination light source essentially continuous in the visible spectral range and formed by light emitting diodes, the illumination light source including at least one white light emitting diode, a collecting arrangement also housed in the measurement head for the capturing of measurement light originating from a measurement spot on the sample, a spectrometer optically connected to the collecting arrangement for the splitting of the measurement light captured by the collecting arrangement into its spectral components and for the generation of corresponding electrical measurement signals, and an electronic circuit for the control of the illumination arrangement and the spectrometer as well as for the processing of the electrical measurement signals, the measurement head including an illumination channel for each light emitting diode for directing the light originating from each light emitting diode at a defined angle of incidence onto the measurement spot on the sample and the electronic circuit being constructed for selectively controlling the light emitting diodes forming the illumination light source, and wherein said electronic circuit is effective for individual adjustment of emitted light intensity of each individual light emitting diode.

2. Spectrophotometer according to claim 1, further comprising, apart from the at least one white light emitting diode, additional light emitting diodes with different emission spectra, the electronic circuit being constructed for electronically adjusting the spectrum of the illumination light falling onto the measurement spot of the sample according to the desired measurement conditions by a corresponding control of the individual light emitting diodes.

3. Spectrophotometer according to claim 1, further comprising at least one light emitting diode radiating in the UV range in addition to the white light emitting diode, and the electronic circuit being constructed for electronically adjusting the UV components of the measurement light falling onto the measurement spot of the sample according to the desired measurement conditions, by a corresponding control of the individual light emitting diodes.

4. Spectrophotometer according to claim 1, wherein the illumination channels of the measurement head are grouped into at least two different illumination channel arrangements, whereby the illumination channels belonging to the same illumination channel arrangement respectively illuminate the sample at the same angle of incidence, the angles of incidence being different for each illumination channel arrangement, and the electronic control is constructed to separately control the light emitting diodes of the individual illumination channel arrangements so that the sample to be measured can be selectively illuminated, and wherein the light emitting diodes (LEDs) are concentrically, circularly positioned, the concentrical circular arrangement and the illumination channel arrangement allowing for different illumination angles.

5. Spectrophotometer according to claim 1, wherein the collector arrangement includes a telecentrical imaging system for the capturing of the measurement light originating from the measurement spot of the sample.

6. Spectrophotometer according to claim 1, wherein the measurement head is provided with capturing means for capturing the distance between the measurement head and the sample to be measured, and the electronic circuit is constructed to cooperate with the distance measuring means for generating distance correction values from the captured distance for the measurement data obtained during the measurement of the sample.

7. Spectrophotometer according to claim 6, wherein the distance measurement is made according to a mode selected from the group of:
   a) a distance measurement at the same location as the color measurement;
   b) a distance measurement with an illumination lens system that is the same as an illumination lens system for the color measurement;
   c) a distance measurement with the same collecting channel as the color measurement; and
   d) combinations thereof.

8. Spectrophotometer according to claim 1, wherein all illumination channels are of equal construction and mutually corresponding optical components of the individual illumination channels are integrated into a one piece optics component.

9. Spectrophotometer according to claim 8, wherein the optical component of the illumination channels respectively integrated into the one-piece optics component are oriented in the measurement head by way of mechanical positioning structures.

10. A method comprising the step of using the spectrophotometer according to claim 1 as built-in sensor in at least one of an automated color measurement system and an automated color printing system.

11. A method comprising the step of using the spectrophotometer according to claim 4 for the colorimetric measurement of a sample under different illumination angles and for the production of corresponding multi-angle measurement data.

12. A method comprising the step of using the spectrophotometer according to claim 4 for the colorimetric measurement of a sample under different illumination angles and for the production of multi-angle device profiles for a color management system.

13. Color densitometer, comprising a measurement head, an illumination arrangement housed in the measurement head for illuminating a sample to be measured, the illumination arrangement having an illumination light source formed by at least one red, one blue and one green light emitting diode, a collecting arrangement for capturing measurement light originating from a measurement spot on the sample and also housed in the measurement head, a photoreceiver optically connected with the collecting arrangement for producing electrical measurement signals corresponding to the measurement light captured by the collecting arrangement, and an electronic circuit for the control of the illumination arrangement and the photoreceiver as well as for the processing of the electrical measurement signals, the measurement head having a separate illumination channel for each light emitting diode for directing the light originating from each light emitting diode under a defined angle of incidence onto the measurement spot on the sample, the electronic circuit being constructed for selectively controlling the light emitting diodes forming the illumination light source, the photoreceiver being constructed as a spectrometer for dividing the measurement light guided thereto into its spectral components and converting it into electrical measurement signals corresponding to the spectral components, the spectrometer including different predefined density filter functions as spectral value tables, and being constructed for calculating density values from the spectral measurement signals and the spectral value tables.

14. A method for the measurement of light remitted or emitted from a sample, comprising:

a) providing a sample to be measured;

b) providing a spectrophotometer for use in measuring light remitted or emitted from the sample, the spectrophotometer including a measurement head, an illumination arrangement for the sample to be measured, the illumination arrangement being housed in the measurement head and having an illumination light source essentially continuous in the visible spectral range and formed by light emitting diodes, the illumination light source including at least one white light emitting diode, a collecting arrangement also housed in the measurement head for the capturing of measurement light originating from a measurement spot on the sample, a spectrometer optically connected to the collecting arrangement for splitting of the measurement light captured by the collecting arrangement in its spectral components and for generation of corresponding electrical measurement signals, and an electronic circuit for control of the illumination arrangement and the spectrometer for the processing of the electrical measurement signals, the measurement head including an illumination channel for each light emitting diode for directing the light originating from each light emitting diode at a defined angle of incidence onto the measurement spot on the sample and the electronic circuit being constructed for selectively controlling the light emitting diodes forming the illumination light source;

c) individually adjusting the emitted light intensity for individual light emitting diodes; and d) obtaining a measurement of light remitted or emitted from the sample using the spectrophotometer.

15. Method according to claim 14, wherein the spectrophotometer is provided as a built-in sensor in at least one of an automated color measurement system and an automated color printing system.

16. Method according to claim 14, wherein the light measurement generates colorimetric measurement data for the sample under different illumination angles.

17. Method according to claim 16, further comprising using the colorimetric measurement data to produce corresponding multi-angle measurement data.

18. Method according to claim 16, further comprising using the colorimetric measurement data to produce multi-angle device profiles for a color management system.

* * * * *